US012195468B2

United States Patent
Xu et al.

(10) Patent No.: US 12,195,468 B2
(45) Date of Patent: Jan. 14, 2025

(54) TLR7 AGONIST FOR TREATING COLORECTAL CANCER AND PHARMACEUTICAL COMBINATION THEREOF

(71) Applicant: CHIA TAI TIANQING PHARMACEUTICAL GROUP CO., LTD., Lianyungang (CN)

(72) Inventors: Hongjiang Xu, Lianyungang (CN); Mincheng Zhang, Lianyungang (CN); Ying Zhang, Lianyungang (CN); Wei Song, Lianyungang (CN); Ling Yang, Lianyungang (CN); Xiquan Zhang, Lianyungang (CN)

(73) Assignee: CHIA TAI TIANQING PHARMACEUTICAL GROUP CO., LTD., Lianyungang (CN)

(*) Notice: Subject to any disclaimer, the term of this patent is extended or adjusted under 35 U.S.C. 154(b) by 818 days.

(21) Appl. No.: 17/284,436

(22) PCT Filed: Oct. 12, 2019

(86) PCT No.: PCT/CN2019/110824
§ 371 (c)(1),
(2) Date: Apr. 9, 2021

(87) PCT Pub. No.: WO2020/074006
PCT Pub. Date: Apr. 16, 2020

(65) Prior Publication Data
US 2022/0235053 A1   Jul. 28, 2022

(30) Foreign Application Priority Data
Oct. 12, 2018   (CN) .......................... 201811187837.6

(51) Int. Cl.
*C07D 487/04*   (2006.01)
*A61P 35/00*   (2006.01)

(52) U.S. Cl.
CPC ............ *C07D 487/04* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 2017/0273983 A1* | 9/2017 | Ding | .................... | C07D 487/04 |
| 2018/0161318 A1 | 6/2018 | Kim et al. | | |
| 2018/0370976 A1 | 12/2018 | Ding et al. | | |

FOREIGN PATENT DOCUMENTS

| WO | 2010033074 A1 | 3/2010 | | |
|---|---|---|---|---|
| WO | WO-2016023511 A1 * | 2/2016 | ........... | A61K 31/519 |
| WO | 2017/076346 A1 | 5/2017 | | |

OTHER PUBLICATIONS

Ahmed et al, "Advances in the management of colorectal cancer: from biology to treatment", 2014, International Journal of Colorectal Disease, 29, pp. 1031-1042 (Year: 2014).*

Shen et al, "Anlotinib: a novel multi-targeting tyrosine kinase inhibitor in clinical development", 2018, Journal of Hematology & Oncology, 11, pp. 1-11 (Year: 2018).*

Wang et al, "The TLR7 agonist induces tumor regression both by promoting CD4+T cells proliferation and by reversing T regulatory cell mediated suppression via dendritic cells", 2014, 6, pp. 1779-1789 (Year: 2014).*

Xie et al, "Preclinical characterization of anlotinib, a highly potent and selective vascular endothelial growth factor receptor-2 inhibitor", 2018, Cancer Science, 109, pp. 1207-1219 (Year: 2018).*

NCI Dictionary of Cancer Terms, "Synergistic", National Cancer Institute, Accessed May 21, 2024 (Year: 2024).*

Moradi-Marjaneh, et al; Toll Like Receptor Signaling Pathway as a Potential Therapeutic Target in Colorectal Cancer; Jour.Cell.Phys.; vol. 233,No. 8; Nov. 18, 2017; 5613-5622.

Shen, et al; Anlotinib: a novel multi-targeting tyrosine kinase inhibitor in clinical development; Jour.Hematology & Oncology; 2018; 11:120; 1-11.

ISA/CN; International Search Report; PCT/CN2019/110824; mailed Jan. 14, 2020.

Eiró et al., "Toll-like Receptor-4 Expression by Stromal Fibroblasts Is Associated with Poor Prognosis in Colorectal Cancer", J. Immunother., vol. 36, No. 6, Jul./Aug. 2013, pp. 342-349.

Beilmann-Lehtonen et al., "High Tissue TLR5 Expression Predicts Better Outcomes in Colorectal Cancer Patients", Oncology, vol. 99, No. 9, 2021, pp. 589-600.

(Continued)

*Primary Examiner* — Mark L Shibuya
*Assistant Examiner* — Madeline E Braun
(74) *Attorney, Agent, or Firm* — Kilpatrick Townsend & Stockton LLP

(57) ABSTRACT

Disclosed are a compound of formula I as a toll-like receptor 7 (TLR7) agonist or a pharmaceutically acceptable salt thereof for treating colorectal cancer, a pharmaceutical combination for treating colorectal cancer comprising the TLR7 agonist and a tyrosine kinase inhibitor, and the use of the compound of formula I or the pharmaceutically acceptable salt thereof and the pharmaceutical combination for treating colorectal cancer.

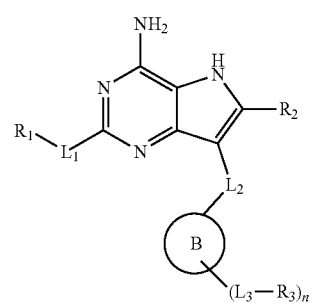

I

15 Claims, No Drawings

(56) References Cited

OTHER PUBLICATIONS

Koga-Yamakawa et al., "Intratracheal and oral administration of SM-276001: A selective TLR7 agonist, leads to antitumor efficacy in primary and metastatic models of cancer", International Journal of Cancer, vol. 132, No. 3, Jul. 11, 2012, pp. 580-590.

* cited by examiner

TLR7 AGONIST FOR TREATING COLORECTAL CANCER AND PHARMACEUTICAL COMBINATION THEREOF

CROSS-REFERENCE TO RELATED APPLICATIONS

The present application is a § 371 National Phase Application of PCT/CN2019/110824, filed on Oct. 12, 2019, which application claims the benefit and priority under Article 8 of the PCT to the Chinese Patent Application No. 201811187837.6, filed towards China National Intellectual Property Administration on Oct. 12, 2018, the entire contents of which are incorporated herein by reference in their entireties for all purposes herein.

TECHNICAL FIELD

The present application relates to a TLR7 agonist and a pharmaceutical combination thereof for use in treating colorectal cancer. In particular, the present application relates to use of a toll-like receptor 7 (TLR7) agonist in treating colorectal cancer, a pharmaceutical combination of the agonist and a tyrosine kinase inhibitor, and use of the pharmaceutical combination in treating colorectal cancer.

BACKGROUND

Tyrosine kinase is a group of enzymes which catalyze the phosphorylation of tyrosine residues in proteins. It plays an important role in intracellular signal transduction, takes part in adjustment, signaling and development of normal cells, and is closely related to proliferation, differentiation, migration and apoptosis of tumor cells. Many receptor tyrosine kinases are related to formation of tumor and can be classified as epidermal growth factor receptor (EGFR), platelet-derived growth factor receptor (PDGFR), vascular endothelial growth factor receptor (VEGFR), fibroblast growth factor receptor (FGFR) and the like according to the structure of extracellular domain.

Toll-like receptor is expressed in a variety of immune cells. Toll-like receptors recognize highly conserved structural motifs: pathogen associated molecular patterns (PAMPs) expressed by microbial pathogens or damage associated molecular patterns (DAMPs) released by necrotic cells. Toll-like receptors are stimulated by corresponding PAMPs or DAMPs to induce signaling cascade, resulting in activation of transcription factors such as AP-1, NF-κB and an interferon regulation factor (an impulse response function). As such, a variety of cellular reactions are induced, including production of interferons, proinflammatory cytokines and effector cytokines, thus promoting immune response. 13 Toll-like receptors have been found in mammals so far. Toll-like receptors 1, 2, 4, 5 and 6 are mainly expressed on cell surfaces and toll-like receptors 3, 7, 8 and 9 are expressed in endosomes. Different toll-like receptors recognize ligands derived from different pathogens. Toll-like receptor 7 (TLR7) is mainly expressed in plasmacytoid dendritic cells (pDCs), and induces secretion of the interferon alpha (IFN-alpha) by ligand recognition. Some TLR7 agonists have been reported, for example, imiquimod, resiquimod, GS-9620 and the like. WO2016023511 and WO2017076346, the content of which are incorporated herein by reference in their entirety, disclose a class of novel TLR7 agonists demonstrating good bioactivity and selectivity.

The role of TLR7 in tumors has been studied. Imiquimod is a TLR7 agonist approved by US FDA for treating external genital warts, actinic ketatosis and superficial basal cell carcinoma. Imiquimod can promote immune responses of the body and also can be used as an adjuvant to enhance the efficacy of radiotherapy. However, TLR7 agonists are not suitable to all tumors.

Although patients with proliferative diseases (for example, cancers) have many treatment options, there's still a need for more effective therapeutic agents for clinical use, in particular combined use of two or more drugs.

BRIEF SUMMARY

In one aspect, the present application provides a compound of formula I or a pharmaceutically acceptable salt thereof for use in treating colorectal cancer, or a pharmaceutical composition comprising the compound of formula I or the pharmaceutically acceptable salt thereof for use in treating colorectal cancer.

In another aspect, the present application further provides use of the compound of formula I or the pharmaceutically acceptable salt thereof in preparing a medicament for treating colorectal cancer.

The present application further provides a method for treating colorectal cancer, comprising administering to a subject in need thereof an effective amount of the compound of formula I or the pharmaceutically acceptable salt thereof. The present application further provides use of the compound of formula I or the pharmaceutically acceptable salt thereof in treating colorectal cancer.

In the second aspect, the present application provides a pharmaceutical combination comprising a TLR7 agonist and anlotinib.

In another aspect, the present application further provides use of the pharmaceutical combination disclosed herein in preparing a medicament for treating colorectal cancer. The present application further provides a method for treating colorectal cancer, comprising administering to a subject in need thereof an effective amount of the pharmaceutical combination disclosed herein. The present application further provides a pharmaceutical combination disclosed herein for use in treating colorectal cancer. The present application further provides use of the pharmaceutical combination disclosed herein in treating colorectal cancer. The pharmaceutical combination disclosed herein comprises the TLR7 agonist and anlotinib.

SUMMARY

In one aspect, the present application provides a compound of formula I or a pharmaceutically acceptable salt thereof for use in treating colorectal cancer, or a pharmaceutical composition comprising a compound of formula I or a pharmaceutically acceptable salt thereof for use in treating colorectal cancer, wherein the compound of formula I is:

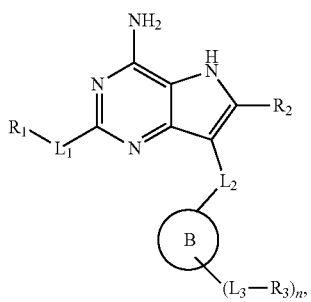

wherein, $L_1$ and $L_2$ are each independently selected from the group consisting of —O—, —CH$_2$—, —S—, —NH—, —NHC(=O)—, —C(=O)—, —C(=O)NH—, —S(=O)—, —S(=O)$_2$—, —NHS(=O)$_2$— and —S(=O)$_2$NH—, wherein the —CH$_2$—, —NH—, —NHC(=O)—, —C(=O)NH—, —NHS(=O)$_2$— or —S(=O)$_2$NH— is optionally substituted with one or more $R_4$;

$R_1$ is selected from the group consisting of hydrogen, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, 3-10 membered aryl and 3-10 membered heteroaryl, wherein the $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, 3-10 membered aryl and 3-10 membered heteroaryl are optionally substituted with one or more $R_4$;

$R_2$ is selected from the group consisting of hydrogen, halogen, cyano, hydroxyl, sulfydryl, amino, —COOH, —CONH$_2$, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, 3-10 membered aryl and 3-10 membered heteroaryl, wherein the hydroxyl, sulfydryl, amino, —COOH, —CONH$_2$, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, 3-10 membered aryl and 3-10 membered heteroaryl are optionally substituted with one or more $R_4$;

B is selected from the group consisting of $C_{3-10}$ cyclohydrocarbyl, 3-10 membered heterocyclohydrocarbyl, 3-10 membered aryl and 3-10 membered heteroaryl; $L_3$ is selected from the group consisting of a bond, $C_{0-6}$ alkylene, imino, —O—, —S—, —S(=O)— and —S(=O)$_2$—, wherein the $C_{0-6}$ alkylene and imino are optionally substituted with one or more $R_4$;

$R_3$ is selected from the group consisting of hydrogen, amino, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, 3-10 membered aryl and 3-10 membered heteroaryl, wherein the amino, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, 3-10 membered aryl and 3-10 membered heteroaryl are optionally substituted with one or more $R_4$, or $R_3$ and $L_3$, together with an adjacent atom on ring B, form a saturated or unsaturated 5-8 membered ring optionally substituted with one or more $R_4$;

n is 0, 1, 2, 3, 4 or 5;

$R_4$ is selected from the group consisting of halogen, cyano, —R, —OR, =O, —SR, —NR$_2$, =NR, —C(halogen)$_3$, —CR(halogen)$_2$, —CR$_2$(halogen), —OCN, —SCN, —N=C=O, —NCS, —NO, —NO$_2$, —NRC(=O)R, —NRC(=O)OR, —NRC(=O)NRR, —C(=O)NRR, —C(=O)OR, —OC(=O)NRR, —OC(=O)OR, —C(=O)R, —S(=O)$_2$OR, —S(=O)$_2$R, —OS(=O)$_2$OR, —S(=O)$_2$NRR, —S(=O)R, —NRS(=O)$_2$R, —NRS(=O)$_2$NRR, —NRS(=O)$_2$OR, —OP(=O)(OR)$_2$, —P(=O)(OR)$_2$, —C(=O)R, —C(=S)R, —C(=O)OR, —C(=S)OR, —C(=O)SR, —C(=S)SR, —C(=O)NRR, —C(=S)NRR, —C(=NR)NRR and —NRC(=NR)NRR; each R is independently selected from the group consisting of H, $C_{1-8}$ alkyl, $C_{3-8}$ cyclohydrocarbyl, 3-8 membered heterocyclohydrocarbyl, 3-8 membered aryl, 3-8 membered heteroaryl, 3-8 membered arylalkyl and 3-8 membered heteroarylalkyl;

and when $L_1$ is —CH$_2$— or —NH—, $R_3$ is not H;

or a pharmaceutically acceptable salt thereof.

In some embodiments of the present application, the compound of formula I or the pharmaceutically acceptable salt thereof may have a structure shown as follows.

In some embodiments of the compound of formula I, $L_1$ and $L_2$ are each independently selected from the group consisting of —O—, —CH$_2$—, —S—, —NH—, —C(=O)—, —S(=O)— and —S(=O)$_2$—, wherein the —CH$_2$— and —NH— are optionally substituted with one or more $R_4$. In some embodiments of the compound of formula I, $L_1$ and $L_2$ are each independently selected from the group consisting of —O—, —CH$_2$—, —S—, and —NH—, wherein the —CH$_2$— and —NH— are optionally substituted with one or more $R_4$. In some embodiments of the compound of formula I, $L_1$ and $L_2$ are each independently selected from the group consisting of —O— and —CH$_2$—, wherein the —CH$_2$— is optionally substituted with one or more $R_4$.

In some embodiments of the compound of formula I, $R_1$ is selected from the group consisting of hydrogen, $C_{1-6}$ alkyl, $C_{2-6}$ alkenyl, $C_{2-6}$ alkynyl, $C_{3-6}$ cyclohydrocarbyl, 3-6 membered heterocyclohydrocarbyl, 3-6 membered aryl and 3-6 membered heteroaryl, wherein the $C_{1-6}$ alkyl, $C_{2-6}$ alkenyl, $C_{2-6}$ alkynyl, $C_{3-6}$ cyclohydrocarbyl, 3-6 membered heterocyclohydrocarbyl, 3-6 membered aryl and 3-6 membered heteroaryl are optionally substituted with one or more $R_4$. In some embodiments of the compound of formula I, $R_1$ is selected from the group consisting of $C_{1-6}$ alkyl, wherein the $C_{1-6}$ alkyl is optionally substituted with one or more $R_4$.

In some embodiments of the compound of formula I, $R_2$ is selected from the group consisting of hydrogen, halogen, cyano, hydroxyl, sulfydryl, amino, —COOH, —CONH$_2$, $C_{1-6}$ alkyl, $C_{2-6}$ alkenyl, $C_2$-6 alkynyl, $C_{3-6}$ cyclohydrocarbyl, 3-6 membered heterocyclohydrocarbyl, 3-6 membered aryl and 3-6 membered heteroaryl, wherein the hydroxyl, sulfydryl, amino, —COOH, —CONH$_2$, $C_{1-6}$ alkyl, $C_{2-6}$ alkenyl, $C_{2-6}$ alkynyl, $C_{3-6}$ cyclohydrocarbyl, 3-6 membered heterocyclohydrocarbyl, 3-6 membered aryl and 3-6 membered heteroaryl are optionally substituted with one or more $R_4$. In some embodiments of the compound of formula I, $R_2$ is selected from the group consisting of hydrogen, halogen, cyano, hydroxyl, amino, —CONH$_2$ and $C_{1-6}$ alkyl, wherein the hydroxyl, amino, —CONH$_2$ and $C_{1-6}$ alkyl are optionally substituted with one or more $R_4$. In some embodiments of the compound of formula I, $R_2$ is selected from the group consisting of hydrogen, cyano and —CONH$_2$, wherein the —CONH$_2$ is optionally substituted with one or more $R_4$.

In some embodiments of the compound of formula I, B is selected from the group consisting of 3-10 membered aryl and 3-10 membered heteroaryl. In some embodiments of the compound of formula I, B is selected from the group consisting of 5-7 membered aryl and 5-7 membered heteroaryl. In some embodiments of the compound of formula I, B is selected from the group consisting of phenyl, pyridinyl, pyrimidinyl, pyridazinyl, pyrazinyl, thienyl, thiazolyl, furanyl, oxazolyl, thiadiazolyl, isoxazolyl, oxadiazolyl, pyrrolyl, imidazolyl, pyrazolyl, isothiazolyl and triazolyl. In some embodiments of the compound of formula I, B is selected from the group consisting of phenyl, pyridinyl and thiazolyl.

In some embodiments of the compound of formula I, $L_3$ is selected from the group consisting of a bond and $C_{0-6}$ alkylene, wherein the $C_{0-6}$ alkylene is optionally substituted with one or more $R_4$.

In some embodiments of the compound of formula I, $R_3$ is selected from the group consisting of hydrogen, amino, $C_{1-6}$ alkyl, $C_{2-6}$ alkenyl, $C_{2-6}$ alkynyl, $C_{3-8}$ cyclohydrocarbyl, 3-8 membered heterocyclohydrocarbyl, 3-8 membered aryl and 3-8 membered heteroaryl, wherein the amino, $C_{1-6}$ alkyl, $C_{2-6}$ alkenyl, $C_{2-6}$ alkynyl, $C_{3-8}$ cyclohydrocarbyl, 3-8 membered heterocyclohydrocarbyl, 3-8 membered aryl and 3-8 membered heteroaryl are optionally substituted with one or more $R_4$; or $R_3$ and $L_3$, together with adjacent atoms on ring B, form a saturated or unsaturated 5-8 membered ring optionally substituted with one or more $R_4$. In some embodiments of the compound of formula I, $R_3$ is selected from the group consisting of hydrogen, amino, $C_{1-6}$ alkyl, $C_{3-8}$ cyclohydrocarbyl, 3-8 membered heterocyclohydrocarbyl, 3-8 membered aryl and 3-8 membered heteroaryl, wherein the amino, $C_{1-6}$ alkyl, $C_{3-8}$ cyclohydrocarbyl, 3-8 membered heterocyclohydrocarbyl, 3-8 membered aryl and 3-8 membered heteroaryl are optionally substituted with one or more $R_4$; or $R_3$ and $L_3$, together with adjacent atoms on ring B, form a saturated or unsaturated 5-8 membered ring optionally substituted with one or more $R_4$. In some embodiments of the compound of formula I, $R_3$ is selected from the group consisting of hydrogen, amino, $C_{1-6}$ alkyl, piperazinyl, morpholinyl, tetrahydropyrrolyl, piperidinyl, azetidinyl, diazepanyl and 2-oxa-5-azabicyclo[2.2.1]heptyl, wherein the amino, $C_{1-6}$ alkyl, piperazinyl, morpholinyl, tetrahydropyrrolyl, piperidinyl, azetidinyl, diazepanyl and 2-oxa-5-azabicyclo[2.2.1]heptyl are optionally substituted with one or more $R_4$; or $R_3$ and $L_3$, together with adjacent atoms on ring B, form a saturated or unsaturated 6 membered ring optionally substituted with one or more $R_4$.

In some embodiments of the compound of formula I, $R_4$ is selected from the group consisting of halogen, cyano, —R, —OR, =O, —SR, —NR$_2$, =NR, —C(halogen)$_3$, —CR(halogen)$_2$, —CR$_2$(halogen), —OCN, —SCN, —N=C=O, —NCS, —NO, —NO$_2$, —NRC(=O)R, —C(=O)NRR, —C(=O)OR, —OC(=O)NRR, —C(=O)R, —S(=O)$_2$OR, —S(=O)$_2$R, —OS(=O)$_2$OR, —S(=O)$_2$NRR, —S(=O)R, —NRS(=O)$_2$R, —C(=O)R, —C(=O)OR and —C(=O)NRR. In some embodiments of the compound of formula I, $R_4$ is selected from the group consisting of halogen, cyano, —R, —OR, =O, —NR$_2$, =NR, —C(halogen)$_3$, —CR(halogen)$_2$ and —CR$_2$(halogen). In some embodiments of the compound of formula I, $R_4$ is selected from the group consisting of halogen, —R, —OR and =O. In the embodiments, each R is independently selected from the group consisting of H, $C_{1-8}$ alkyl, $C_{3-8}$ cyclohydrocarbyl, 3-8 membered heterocyclohydrocarbyl, 3-8 membered aryl, 3-8 membered heteroaryl, 3-8 membered arylalkyl and 3-8 membered heteroarylalkyl.

In some embodiments of the present application, the compound of formula I or the pharmaceutically acceptable salt thereof is selected from one or more of the following compounds or pharmaceutically acceptable salts thereof.

2-butoxy-7-(3-((4-methylpiperazin-1-yl)methyl)benzyl)-5H-pyrrolo[3,2-d]pyrimidin-4-amine;
2-butoxy-7-(3-(morpholinomethyl)benzyl)-5H-pyrrolo[3,2-d]pyrimidin-4-amine;
7-(3-(aminomethyl)benzyl)-2-butoxy-5H-pyrrolo[3,2-d]pyrimidin-4-amine;
2-butoxy-7-(3-(pyrrolidin-1-ylmethyl)benzyl)-5H-pyrrolo[3,2-d]pyrimidin-4-amine;
2-butoxy-7-(4-((3,3-difluoropyrrolidin-1-yl)methyl)benzyl)-5H-pyrrolo[3,2-d]pyrimidin-4-amine;
2-butoxy-7-(4-((3-fluoropyrrolidin-1-yl)methyl)benzyl)-5H-pyrrolo[3,2-d]pyrimidin-4-amine;
1-(4-((4-amino-2-butoxy-5H-pyrrolo[3,2-d]pyrimidin-7-yl)methyl)benzyl)pyrrolidin-3-ol;
2-butoxy-7-(4-(piperidin-1-ylmethyl)benzyl)-5H-pyrrolo[3,2-d]pyrimidin-4-amine;
2-butoxy-7-(4-(morpholinomethyl)benzyl)-5H-pyrrolo[3,2-d]pyrimidin-4-amine;
2-butoxy-7-(4-((4-methylpiperazin-1-yl)methyl)benzyl)-5H-pyrrolo[3,2-d]pyrimidin-4-amine;
2-butoxy-7-(4-((dimethylamino)methyl)benzyl)-5H-pyrrolo[3,2-d]pyrimidin-4-amine;
2-butoxy-7-(4-((diethylamino)methyl)benzyl)-5H-pyrrolo[3,2-d]pyrimidin-4-amine;
2-butoxy-7-(4-((dipropylamino)methyl)benzyl)-5H-pyrrolo[3,2-d]pyrimidin-4-amine;
7-(4-(azetidin-1-ylmethyl)benzyl)-2-butoxy-5H-pyrrolo[3,2-d]pyrimidin-4-amine;
2-butoxy-7-(4-((3-methoxyazetidin-1-yl)methyl)benzyl)-5H-pyrrolo[3,2-d]pyrimidin-4-amine;
2-butoxy-7-(4-((4-methyl-1,4-diazepan-1-yl)methyl)benzyl)-5H-pyrrolo[3,2-d]pyrimidin-4-amine;
2-butoxy-7-(4-((2,6-dimethylmorpholino)methyl)benzyl)-5H-pyrrolo[3,2-d]pyrimidin-4-amine;
7-(4-(((1S,4S)-2-oxa-5-azabicyclo[2.2.1]heptan-5-yl)methyl)benzyl)-2-butoxy-5H-pyrrolo[3,2-d]pyrimidin-4-amine;
2-butoxy-7-(4-((4-methoxypiperidin-1-yl)methyl)benzyl)-5H-pyrrolo[3,2-d]pyrimidin-4-amine;
2-butoxy-7-(4-((4-isopropylpiperazin-1-yl)methyl)benzyl)-5H-pyrrolo[3,2-d]pyrimidin-4-amine;
2-butoxy-7-(4-(pyrrolidin-1-ylmethyl)benzyl)-5H-pyrrolo[3,2-d]pyrimidin-4-amine;
2-butoxy-7-((6-(pyrrolidin-1-ylmethyl)pyridin-3-yl)methyl)-5H-pyrrolo[3,2-d]pyrimidin-4-amine;
2-butoxy-7-(3-(2-(pyrrolidin-1-yl)ethyl)benzyl)-5H-pyrrolo[3,2-d]pyrimidin-4-amine;
2-butoxy-7-(4-(1-(pyrrolidin-1-yl)ethyl)benzyl)-5H-pyrrolo[3,2-d]pyrimidin-4-amine;
2-butoxy-7-(4-(1-methylpiperidin-4-yl)benzyl)-5H-pyrrolo[3,2-d]pyrimidin-4-amine;
2-butoxy-7-(4-(1-methylpyrrolidin-2-yl)benzyl)-5H-pyrrolo[3,2-d]pyrimidin-4-amine;
1-(4-((4-amino-2-butoxy-5H-pyrrolo[3,2-d]pyrimidin-7-yl)methyl)phenyl)-4-methylpiperazin-2-one;
7-benzyl-2-(2-methoxyethoxy)-5H-pyrrolo[3,2-d]pyrimidin-4-amine;
2-(2-methoxyethoxy)-7-((6-methylpyridin-3-yl)methyl)-5H-pyrrolo[3,2-d]pyrimidin-4-amine;
7-((5-chloropyridin-2-yl)methyl)-2-(2-methoxyethoxy)-5H-pyrrolo[3,2-d]pyrimidin-4-amine;
2-(2-methoxyethoxy)-7-((6-(pyrrolidin-1-ylmethyl)pyridin-3-yl)methyl)-5H-pyrrolo[3,2-d]pyrimidin-4-amine;
1-(4-((4-amino-2-(2-methoxyethoxy)-5H-pyrrolo[3,2-d]pyrimidin-7-yl)methyl)phenyl)-4-methylpiperazin-2-one;
2-butoxy-7-((5-(pyrrolidin-1-ylmethyl)pyridin-2-yl)methyl)-5H-pyrrolo[3,2-d]pyrimidin-4-amine;

4-amino-2-butoxy-7-((6-(pyrrolidin-1-ylmethyl)pyridin-3-yl)methyl)-5H-pyrrolo[3,2-d]pyrimidin-6-carbonitrile;
4-amino-2-butoxy-7-(4-(pyrrolidin-1-ylmethyl)benzyl)-5H-pyrrolo[3,2-d]pyrimidin-6-carbonitrile;
4-amino-2-butoxy-7-(4-(morpholinomethyl)benzyl)-5H-pyrrolo[3,2-d]pyrimidin-6-carbonitrile;
4-amino-2-butoxy-7-(4-((4-methylpiperazin-1-yl)methyl)benzyl)-5H-pyrrolo[3,2-d]pyrimidin-6-carbonitrile;
4-amino-2-butoxy-7-(4-(pyrrolidin-1-ylmethyl)benzyl)-5H-pyrrolo[3,2-d]pyrimidin-6-carboxamide;
2-butoxy-7-((1,2,3,4-tetrahydroisoquinolin-7-yl)methyl)-5H-pyrrolo[3,2-d]pyrimidin-4-amine;
2-butoxy-7-((2-methyl-1,2,3,4-tetrahydroisoquinolin-7-yl)methyl)-5H-pyrrolo[3,2-d]pyrimidin-4-amine;
2-butoxy-7-((2-ethyl-1,2,3,4-tetrahydroisoquinolin-7-yl)methyl)-5H-pyrrolo[3,2-d]pyrimidin-4-amine;
2-butoxy-7-((2-isopropyl-1,2,3,4-tetrahydroisoquinolin-7-yl)methyl)-5H-pyrrolo[3,2-d]pyrimidin-4-amine;
2-butoxy-7-((1,2,3,4-tetrahydroisoquinolin-6-yl)methyl)-5H-pyrrolo[3,2-d]pyrimidin-4-amine;
2-butoxy-7-((2-methyl-1,2,3,4-tetrahydroisoquinolin-6-yl)methyl)-5H-pyrrolo[3,2-d]pyrimidin-4-amine;
2-butoxy-7-((2-ethyl-1,2,3,4-tetrahydroisoquinolin-6-yl)methyl)-5H-pyrrolo[3,2-d]pyrimidin-4-amine; or
2-butoxy-7-((2-(pyrrolidin-1-ylmethyl)thiazol-5-yl)methyl)-5H-pyrrolo[3,2-d]pyrimidin-4-amine;
or a pharmaceutically acceptable salt thereof.

In some embodiments of the present application, the compound of formula I or the pharmaceutically acceptable salt thereof is 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl)thiazol-5-yl)methyl)-5H-pyrrolo[3,2-d]pyrimidin-4-amine or a pharmaceutically acceptable salt thereof. In some embodiments of the present application, the compound of formula I or the pharmaceutically acceptable salt thereof is 2-butoxy-7-(4-(pyrrolidin-1-ylmethyl)benzyl)-5H-pyrrolo[3,2-d]pyrimidin-4-amine or a pharmaceutically acceptable salt thereof.

In another aspect, the present application further provides use of the compound of formula I or the pharmaceutically acceptable salt thereof or a pharmaceutical composition comprising the compound of formula I or the pharmaceutically acceptable salt thereof in preparing a medicament for treating colorectal cancer. The present application further provides a method for treating colorectal cancer, comprising administering to a subject in need thereof an effective amount of the compound of formula I or the pharmaceutically acceptable salt thereof, or a pharmaceutical composition comprising the compound of formula I or the pharmaceutically acceptable salt thereof. The present application further provides use of the compound of formula I or the pharmaceutically acceptable salt thereof or the pharmaceutical composition comprising the compound of formula I or the pharmaceutically acceptable salt thereof in treating colorectal cancer. In some embodiments of the present application, in the use and method, the compound of formula I or the pharmaceutically acceptable salt thereof can form, with anlotinib or a pharmaceutically acceptable salt thereof, a pharmaceutical combination.

In the second aspect, the present application provides a pharmaceutical combination comprising a TLR7 agonist and anlotinib.

In some embodiments of the present application, provided is a pharmaceutical combination comprising the TLR7 agonist and 1 mg/kg/d of anlotinib or a pharmaceutically acceptable salt thereof; in particular, the pharmaceutical combination comprises 20 mg/kg/d of the TLR7 agonist and 1 mg/kg/d of anlotinib or a pharmaceutically acceptable salt thereof. In some embodiments of the present application, provided is a pharmaceutical combination comprising the TLR7 agonist and anlotinib or a pharmaceutically acceptable salt thereof in a unit dosage of 6 mg, 8 mg, 10 mg or 12 mg; in particular, the pharmaceutical combination comprises 0.0001 mg/kg/d to 20 mg/kg/d of the TLR7 agonist and anlotinib or a pharmaceutically acceptable salt thereof in a unit dosage of 6 mg, 8 mg, 10 mg or 12 mg.

In some embodiments of the present application, provided is a pharmaceutical combination comprising the TLR7 agonist and 6 mg/d to 16 mg/d of anlotinib or a pharmaceutically acceptable salt thereof, in particular, the pharmaceutical combination comprises 0.0001 mg/kg/d to 20 mg/kg/d of the TLR7 agonist and anlotinib or a pharmaceutically acceptable salt thereof in a unit dosage selected from the group consisting of 6 mg/d, 8 mg/d, 10 mg/d, 12 mg/d, 14 mg/d, 16 mg/d or a range formed by any of the aforementioned values; more particularly, the pharmaceutical combination comprises 0.0001 mg/kg/d to 10 mg/kg/d of the TLR7 agonist and 10 mg/d to 14 mg/d of anlotinib or a pharmaceutically acceptable salt thereof.

In some embodiments of the present application, the TLR7 agonist in the pharmaceutical combination disclosed herein is selected from the group consisting of imiquimod, GSK-2245035, resiquimod, vesatolimod (GS-9620), telratolimod, TMX-202, DSP-0509, RG-7854, loxoribine and the compound of formula I or the pharmaceutically acceptable salt thereof. In some embodiments of the present application, the compound of formula I or the pharmaceutically acceptable salt thereof in the pharmaceutical combination disclosed herein has the aforementioned structure or is selected from one or more of the aforementioned compounds.

In some embodiments of the present application, the TLR7 agonist in the pharmaceutical combination may be one or more TLR7 agonists. As used herein, the term "more" refers to more than one, for example, two, three, four, five or more. For example, in some embodiments of the present application, the TLR7 agonist is selected from one or more of GSK-2245035, vesatolimod, and 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof.

In some embodiments of the present application, the pharmaceutical combination is a fixed combination. In some embodiments of the present application, the fixed combination is in the form of a solid pharmaceutical composition. In some embodiments, the solid pharmaceutical composition is selected from the group consisting of a tablet and a capsule.

In some embodiments of the present application, the pharmaceutical combination is a non-fixed combination. In some embodiments of the present application, the TLR7 agonist and anlotinib in the non-fixed combination are each in the form of a solid pharmaceutical composition. In some embodiments of the present application, the solid pharmaceutical composition is selected from the group consisting of a tablet and a capsule.

In some embodiments of the present application, the TLR7 agonist in the pharmaceutical combination is selected from the group consisting of GSK-2245035, vesatolimod and 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof.

In some embodiments of the present application, the pharmaceutical combination comprises 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof, and anlotinib or a pharmaceutically acceptable salt thereof. In some embodiments of the present application, the pharmaceutical combination disclosed herein comprises 2-butoxy-7-(4-(pyrrolidin-1-ylmethyl)benzyl)-5H-pyrrolo[3,2-d]pyrimidin-4-amine or a pharmaceutically acceptable salt thereof, and anlotinib dihydrochloride.

In some embodiments of the present application, the pharmaceutical combination disclosed herein comprises 0.0001 mg/kg/d to 20 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and 1 mg/kg/d of anlotinib dihydrochloride. In some embodiments of the present application, the pharmaceutical combination disclosed herein comprises 0.001 mg/kg/d to 10 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and 1 mg/kg/d of anlotinib dihydrochloride. In some embodiments of the present application, the pharmaceutical combination disclosed herein comprises 0.0001 mg/kg/d to 20 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and anlotinib dihydrochloride at a dosage of 6 mg, 8 mg, 10 mg or 12 mg once daily. In some embodiments of the present application, the pharmaceutical combination disclosed herein comprises 0.001 mg/kg/d to 10 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and anlotinib dihydrochloride at a dosage of 6 mg, 8 mg, 10 mg or 12 mg once daily. In some embodiments of the present application, the pharmaceutical combination disclosed herein comprises 20 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and 1 mg/kg/d of anlotinib dihydrochloride. In some embodiments of the present application, the pharmaceutical combination disclosed herein comprises 0.0001 mg/kg/time to 20 mg/kg/time of 2-butoxy-7-(4-(pyrrolidin-1-ylmethyl)benzyl)-5H-pyrrolo[3,2-d]pyrimidin-4-amine or a pharmaceutically acceptable salt thereof administered thrice a week, and 1 mg/kg/d of anlotinib dihydrochloride administered for 2 weeks continuously. In some embodiments of the present application, the pharmaceutical combination disclosed herein comprises 0.001 mg/kg/time to 10 mg/kg/time of 2-butoxy-7-(4-(pyrrolidin-1-ylmethyl)benzyl)-5H-pyrrolo[3,2-d]pyrimidin-4-amine or a pharmaceutically acceptable salt thereof administered thrice a week, and 1 mg/kg/d of anlotinib dihydrochloride administered for 2 weeks continuously. In some embodiments of the present application, the pharmaceutical combination disclosed herein comprises 0.0001 mg/kg/time to 20 mg/kg/time of 2-butoxy-7-(4-(pyrrolidin-1-ylmethyl)benzyl)-5H-pyrrolo[3,2-d]pyrimidin-4-amine or a pharmaceutically acceptable salt thereof administered thrice a week, and anlotinib dihydrochloride administered for 2 weeks continuously at a dosage of 6 mg, 8 mg, 10 mg or 12 mg once daily. In some embodiments of the present application, the pharmaceutical combination disclosed herein comprises 0.001 mg/kg/time to 10 mg/kg/time of 2-butoxy-7-(4-(pyrrolidin-1-ylmethyl)benzyl)-5H-pyrrolo[3,2-d]pyrimidin-4-amine or a pharmaceutically acceptable salt thereof administered thrice a week, and anlotinib dihydrochloride administered for 2 weeks continuously at a dosage of 6 mg, 8 mg, 10 mg or 12 mg once daily. In some embodiments of the present application, the pharmaceutical combination disclosed herein comprises 20 mg/kg/time of 2-butoxy-7-(4-(pyrrolidin-1-ylmethyl)benzyl)-5H-pyrrolo[3,2-d]pyrimidin-4-amine administered thrice a week and 1 mg/kg/d of anlotinib dihydrochloride administered for 2 weeks continuously.

In some embodiments of the present application, the pharmaceutical combination disclosed herein comprises 0.0001 mg/kg/d to 20 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and 6 mg/d to 16 mg/d of anlotinib dihydrochloride. In some embodiments of the present application, the pharmaceutical combination disclosed herein comprises 0.001 mg/kg/d to 10 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and anlotinib dihydrochloride in a dosage of 6 mg/d, 8 mg/d, 10 mg/d, 12 mg/d, 14 mg/d, 16 mg/d or a range formed by any of the aforementioned values. In some embodiments of the present application, the pharmaceutical combination disclosed herein comprises 0.001 mg/kg/d to 10 mg/kg/d of 2-butoxy-7-(4-(pyrrolidin-1-ylmethyl)benzyl)-5H-pyrrolo[3,2-d]pyrimidin-4-amine or a pharmaceutically acceptable salt thereof, and 10 mg/d to 14 mg/d of anlotinib dihydrochloride. In some embodiments of the present application, the pharmaceutical combination disclosed herein comprises 0.0001 mg/kg/dose to 20 mg/kg/dose of 2-butoxy-7-(4-(pyrrolidin-1-ylmethyl)benzyl)-5H-pyrrolo[3,2-d]pyrimidin-4-amine or a pharmaceutically acceptable salt thereof administered thrice a week, and 6 mg/d to 16 mg/d of anlotinib dihydrochloride administered for 2 weeks continuously. In some embodiments of the present application, the pharmaceutical combination disclosed herein comprises 0.001 mg/kg/time to 10 mg/kg/time of 2-butoxy-7-(4-(pyrrolidin-1-ylmethyl)benzyl)-5H-pyrrolo[3,2-d]pyrimidin-4-amine or a pharmaceutically acceptable salt thereof administered thrice a week, and anlotinib dihydrochloride in a dosage of 6 mg/d, 8 mg/d, 10 mg/d, 12 mg/d, 14 mg/d, 16 mg/d or a range formed by any of the aforementioned values administered for 2 weeks continuously. In some embodiments of the present application, the pharmaceutical combination disclosed herein comprises 0.001 mg/kg/time to 10 mg/kg/time of 2-butoxy-7-(4-(pyrrolidin-1-ylmethyl)benzyl)-5H-pyrrolo[3,2-d]pyrimidin-4-amine or a pharmaceutically acceptable salt thereof administered thrice a week, and 10 mg/d to 14 mg/d of anlotinib dihydrochloride administered for 2 weeks continuously.

In another aspect, the present application further provides use of the pharmaceutical combination disclosed herein in preparing a medicament for treating colorectal cancer. The present application further provides a method for treating colorectal cancer, comprising administering to a subject in need thereof an effective amount of the pharmaceutical combination disclosed herein. The present application further provides a pharmaceutical combination disclosed herein for use in treating colorectal cancer. The present application further provides use of the pharmaceutical combination disclosed herein in treating colorectal cancer. The pharmaceutical combination comprises a TLR7 agonist and anlotinib. In some embodiments of the present application, the TLR7 agonist is selected from the group consisting of imiquimod, GSK-2245035, resiquimod, vesatolimod (GS-9620), telratolimod, TMX-202, DSP-0509, RG-7854, loxoribine and a compound of formula I or a pharmaceutically acceptable salt thereof, wherein the compound of formula I or the pharmaceutically acceptable salt thereof has an aforementioned structure or is selected from one or more of the aforementioned compounds. In some embodiments of the present application, the TLR7 agonist is selected from one or more of GSK-2245035, vesatolimod, and 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl)thiazol-5-yl)methyl)-5H-pyrrolo[3,2-d]pyrimidin-4-amine, or a pharmaceutically acceptable salt thereof. In some embodiments of the present application, the TLR7 agonist is selected from 2-butoxy-7-(4-(pyrrolidin-1-ylmethyl)benzyl)-5H-pyrrolo[3,2-d]pyrimidin-4-amine or 2-butoxy-7-((2-(pyrrolidin-1-ylmethyl) thiazol-5-yl)methyl)-5H-pyrrolo[3,2-d]pyrimidin-4-amine, or a pharmaceutically acceptable salt thereof. In some embodiments of the present application, the TLR7 agonist is 2-butoxy-7-(4-(pyrrolidin-1-ylmethyl)benzyl)-5H-pyrrolo[3,2-d]pyrimidin-4-amine or a pharmaceutically acceptable salt thereof.

In some embodiments of the present application, provided is use of the TLR7 agonist and anlotinib in preparing a combined medicament for treating colorectal cancer, wherein the TLR7 agonist and anlotinib are formulated into pharmaceutical compositions separately.

In some embodiments of the present application, further provided is a kit for use in treating colorectal cancer, comprising (a) a first pharmaceutical composition comprising the TLR7 agonist as the active ingredient, and (b) a second pharmaceutical composition comprising anlotinib as the active ingredient.

In some embodiments of the present application, the colorectal cancer is selected from the group consisting of colon cancer and/or rectal cancer.

Definitions and Description

Unless otherwise stated, the following terms used in the present application shall have the following meanings. A specific term, unless otherwise specifically defined, should not be considered uncertain or unclear, but construed according to its common meaning in the field. When referring to a trade name, it is intended to refer to its corresponding commercial product or its active ingredient.

As used herein, anlotinib has the chemical name of 1-[[[4-(4-fluoro-2-methyl-1H-indol-5-yl)oxy-6-methoxyquinolin-7-yl]oxy]methyl]cyclopropylamine, and the following structural formula:

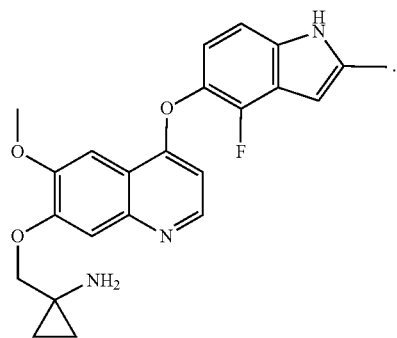

As used herein, names, structural formulas and chemical names of part of the TLR7 agonists are shown in the following table:

| Name/Number | Structural formula | Chemical name |
|---|---|---|
| 1 | | 2-butoxy-7-(3-((4-methylpiperazin-1-yl)methyl)benzyl)-5H-pyrrolo[3,2-d]pyrimidin-4-amine |
| 2 | | 2-butoxy-7-(3-(morpholinomethyl)benzyl)-5H-pyrrolo[3,2-d]pyrimidin-4-amine |
| 3 | | 7-(3-(aminomethyl)benzyl)-2-butoxy-5H-pyrrolo[3,2-d]pyrimidin-4-amine |

-continued

| Name/Number | Structural formula | Chemical name |
|---|---|---|
| 4 | | 2-butoxy-7-(3-(pyrrolidin-1-ylmethyl)benzyl)-5H-pyrrolo[3,2-d]pyrimidin-4-amine |
| 5 | | 2-butoxy-7-(4-((3,3-difluoropyrrolidin-1-yl)methyl)benzyl)-5H-pyrrolo[3,2-d]pyrimidin-4-amine |
| 6 | | 2-butoxy-7-(4-((3-fluoropyrrolidin-1-yl)methyl)benzyl)-5H-pyrrolo[3,2-d]pyrimidin-4-amine |
| 7 | | 1-(4-((4-amino-2-butoxy-5H-pyrrolo[3,2-d]pyrimidin-7-yl)methyl)benzyl)pyrrolidin-3-ol |
| 8 | | 2-butoxy-7-(4-(piperidin-1-ylmethyl)benzyl)-5H-pyrrolo[3,2-d]pyrimidin-4-amine |
| 9 | | 2-butoxy-7-(4-(morpholinomethyl)benzyl)-5H-pyrrolo[3,2-d]pyrimidin-4-amine |

-continued

| Name/Number | Structural formula | Chemical name |
|---|---|---|
| 10 | | 2-butoxy-7-(4-((4-methylpiperazin-1-yl)methyl)benzyl)-5H-pyrrolo[3,2-d]pyrimidin-4-amine |
| 11 | | 2-butoxy-7-(4-((dimethylamino)methyl)benzyl)-5H-pyrrolo[3,2-d]pyrimidin-4-amine |
| 12 | | 2-butoxy-7-(4-((diethylamino)methyl)benzyl)-5H-pyrrolo[3,2-d]pyrimidin-4-amine |
| 13 | | 2-butoxy-7-(4-((dipropylamino)methyl)benzyl)-5H-pyrrolo[3,2-d]pyrimidin-4-amine |
| 14 | | 7-(4-(azetidin-1-ylmethyl)benzyl)-2-butoxy-5H-pyrrolo[3,2-d]pyrimidin-4-amine |
| 15 | | 2-butoxy-7-(4-((3-methoxyazetidin-1-yl)methyl)benzyl)-5H-pyrrolo[3,2-d]pyrimidin-4-amine |

-continued

| Name/Number | Structural formula | Chemical name |
|---|---|---|
| 16 | 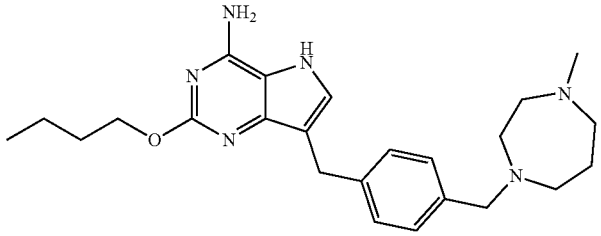 [SMILES: CCCCOc1nc(N)c2[nH]cc(Cc3ccc(CN4CCCN(C)CC4)cc3)c2n1] | 2-butoxy-7-(4-((4-methyl-1,4-diazepan-1-yl)methyl)benzyl)-5H-pyrrolo[3,2-d]pyrimidin-4-amine |
| 17 | 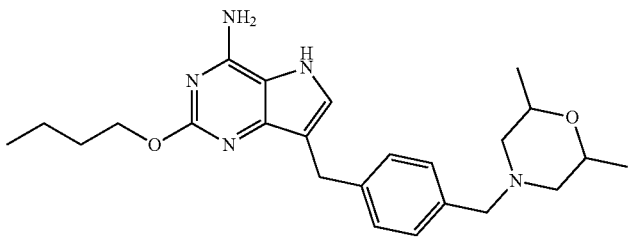 [SMILES: CCCCOc1nc(N)c2[nH]cc(Cc3ccc(CN4CC(C)OC(C)C4)cc3)c2n1] | 2-butoxy-7-(4-((2,6-dimethylmorpholino)methyl)benzyl)-5H-pyrrolo[3,2-d]pyrimidin-4-amine |
| 18 | 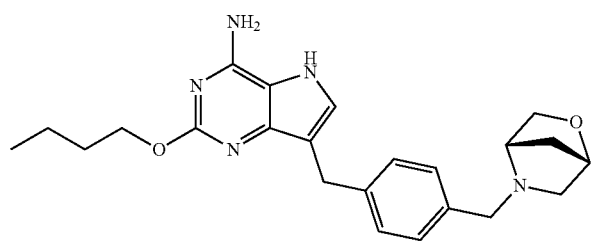 [SMILES: CCCCOc1nc(N)c2[nH]cc(Cc3ccc(CN4C[C@@H]5C[C@H]4CO5)cc3)c2n1] | 7-(4-(((1S,4S)-2-oxa-5-azabicyclo[2.2.1]heptan-5-yl)methyl)benzyl)-2-butoxy-5H-pyrrolo[3,2-d]pyrimidin-4-amine |
| 19 | 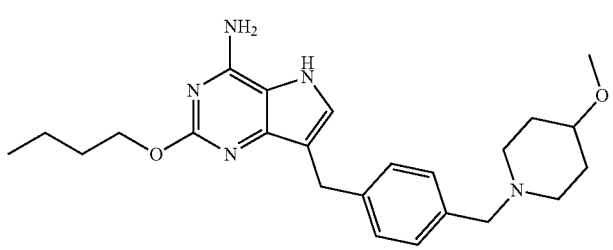 [SMILES: CCCCOc1nc(N)c2[nH]cc(Cc3ccc(CN4CCC(OC)CC4)cc3)c2n1] | 2-butoxy-7-(4-((4-methoxypiperidin-1-yl)methyl)benzyl)-5H-pyrrolo[3,2-d]pyrimidin-4-amine |
| 20 | 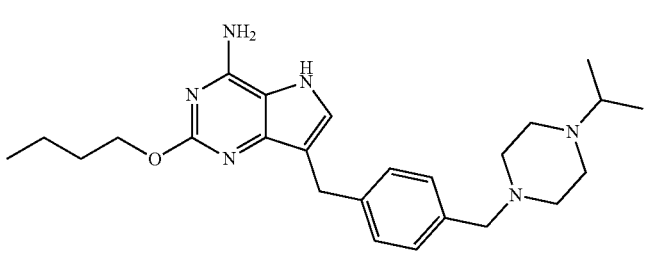 [SMILES: CCCCOc1nc(N)c2[nH]cc(Cc3ccc(CN4CCN(C(C)C)CC4)cc3)c2n1] | 2-butoxy-7-(4-((4-isopropylpiperazin-1-yl)methyl)benzyl)-5H-pyrrolo[3,2-d]pyrimidin-4-amine |
| 21 | 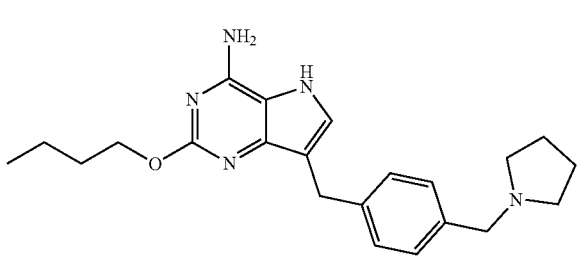 [SMILES: CCCCOc1nc(N)c2[nH]cc(Cc3ccc(CN4CCCC4)cc3)c2n1] | 2-butoxy-7-(4-(pyrrolidin-1-ylmethyl)benzyl)-5H-pyrrolo[3,2-d]pyrimidin-4-amine |

| Name/Number | Structural formula | Chemical name |
|---|---|---|
| 22 | | 2-butoxy-7-((6-(pyrrolidin-1-ylmethyl)pyridin-3-yl)methyl)-5H-pyrrolo[3,2-d]pyrimidin-4-amine |
| 23 | | 2-butoxy-7-(3-(2-(pyrrolidin-1-yl)ethyl)benzyl)-5H-pyrrolo[3,2-d]pyrimidin-4-amine |
| 24 | | 2-butoxy-7-(4-(1-(pyrrolidin-1-yl)ethyl)benzyl)-5H-pyrrolo[3,2-d]pyrimidin-4-amine |
| 25 | | 2-butoxy-7-(4-(1-methylpiperidin-4-yl)benzyl)-5H-pyrrolo[3,2-d]pyrimidin-4-amine |
| 26 | | 2-butoxy-7-(4-(1-methylpyrrolidin-2-yl)benzyl)-5H-pyrrolo[3,2-d]pyrimidin-4-amine |
| 27 | | 1-(4-((4-amino-2-butoxy-5H-pyrrolo[3,2-d]pyrimidin-7-yl)methyl)phenyl)-4-methylpiperazin-2-one |

-continued

| Name/Number | Structural formula | Chemical name |
|---|---|---|
| 28 | | 7-benzyl-2-(2-methoxyethoxy)-5H-pyrrolo[3,2-d]pyrimidin-4-amine |
| 29 | | 2-(2-methoxyethoxy)-7-((6-methylpyridin-3-yl)methyl-5H-pyrrolo[3,2-d]pyrimidin-4-amine |
| 30 | | 7-((5-chloropyridin-2-yl)methyl)-2-(2-methoxyethoxy)-5H-pyrrolo[3,2-d]pyrimidin-4-amine |
| 31 | | 2-(2-methoxyethoxy)-7-((6-(pyrrolidin-1-ylmethyl)pyridin-3-yl)methyl)-5H-pyrrolo[3,2-d]pyrimidin-4-amine |
| 32 | | 1-(4-((4-amino-2-(2-methoxyethoxy)-5H-pyrrolo[3,2-d]pyrimidin-7-yl)methyl)phenyl)-4-methylpiperazin-2-one |
| 33 | | 2-butoxy-7-((5-(pyrrolidin-1-ylmethyl)pyridin-2-yl)methyl)-5H-pyrrolo[3,2-d]pyrimidin-4-amine |

-continued

| Name/Number | Structural formula | Chemical name |
|---|---|---|
| 34 | | 4-amino-2-butoxy-7-((6-(pyrrolidin-1-ylmethyl)pyridin-3-yl)methyl)-5H-pyrrolo[3,2-d]pyrimidin-6-carbonitrile |
| 35 | | 4-amino-2-butoxy-7-(4-(pyrrolidin-1-ylmethyl)benzyl)-5H-pyrrolo[3,2-d]pyrimidin-6-carbonitrile |
| 36 | | 4-amino-2-butoxy-7-(4-(morpholinomethyl)benzyl)-5H-pyrrolo[3,2-d]pyrimidin-6-carbonitrile |
| 37 | | 4-amino-2-butoxy-7-(4-((4-methylpiperazin-1-yl)methyl)benzyl)-5H-pyrrolo[3,2-d]pyrimidin-6-carbonitrile |
| 38 | | 4-amino-2-butoxy-7-(4-(pyrrolidin-1-ylmethyl)benzyl)-5H-pyrrolo[3,2-d]pyrimidin-6-carboxamide |
| 39 | | 2-butoxy-7-((1,2,3,4-tetrahydroisoquinolin-7-yl)methyl)-5H-pyrrolo[3,2-d]pyrimidin-4-amine |

| Name/Number | Structural formula | Chemical name |
|---|---|---|
| 40 | 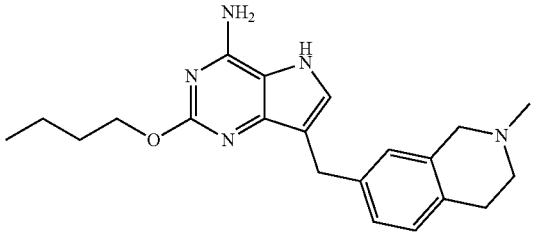 [SMILES: CCCCOc1nc(N)c2[nH]cc(Cc3ccc4c(c3)CN(C)CC4)c2n1] | 2-butoxy-7-((2-methyl-1,2,3,4-tetrahydroisoquinolin-7-yl)methyl)-5H-pyrrolo[3,2-d]pyrimidin-4-amine |
| 41 | 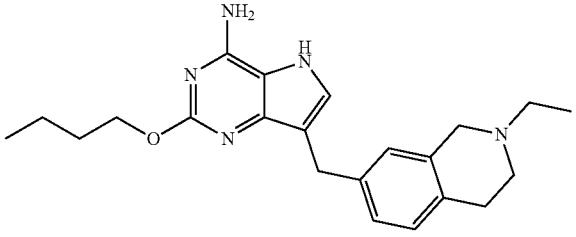 [SMILES: CCCCOc1nc(N)c2[nH]cc(Cc3ccc4c(c3)CN(CC)CC4)c2n1] | 2-butoxy-7-((2-ethyl-1,2,3,4-tetrahydroisoquinolin-7-yl)methyl)-5H-pyrrolo[3,2-d]pyrimidin-4-amine |
| 42 | 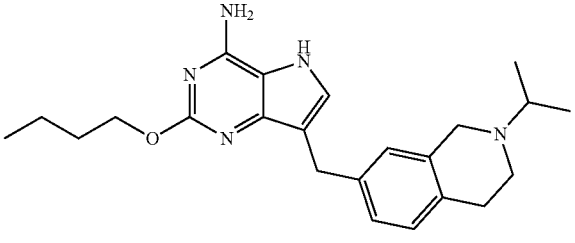 [SMILES: CCCCOc1nc(N)c2[nH]cc(Cc3ccc4c(c3)CN(C(C)C)CC4)c2n1] | 2-butoxy-7-((2-isopropyl-1,2,3,4-tetrahydroisoquinolin-7-yl)methyl)-5H-pyrrolo[3,2-d]pyrimidin-4-amine |
| 43 | 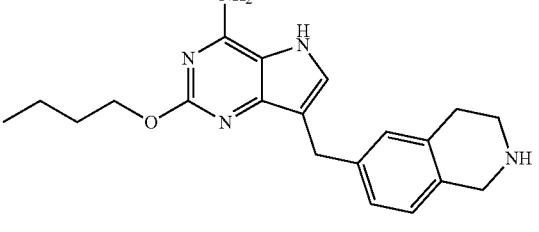 | 2-butoxy-7-((1,2,3,4-tetrahydroisoquinolin-6-yl)methyl)-5H-pyrrolo[3,2-d]pyrimidin-4-amine |
| 44 | 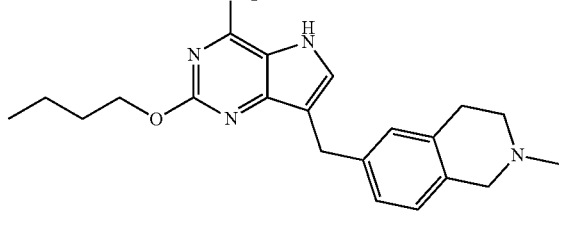 | 2-butoxy-7-((2-methyl-1,2,3,4-tetrahydroisoquinolin-6-yl)methyl)-5H-pyrrolo[3,2-d]pyrimidin-4-amine |
| 45 | 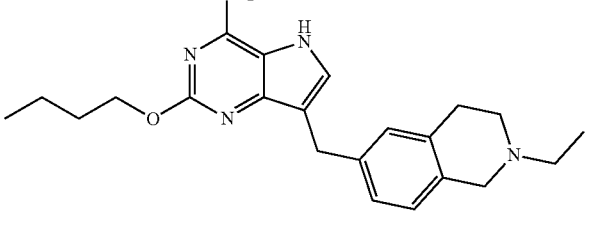 | 2-butoxy-7-((2-ethyl-1,2,3,4-tetrahydroisoquinolin-6-yl)methyl)-5H-pyrrolo[3,2-d]pyrimidin-4-amine |

| Name/Number | Structural formula | Chemical name |
|---|---|---|
| 46 | 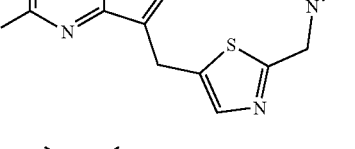 | 2-butoxy-7-((2-(pyrrolidin-1-ylmethyl)thiazol-5-yl)methyl)-5H-pyrrolo[3,2-d]pyrimidin-4-amine |
| Imiquimod | 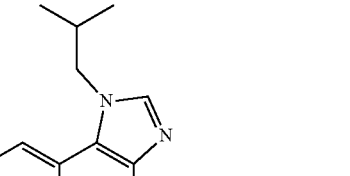 | — |
| GSK-2245035 | 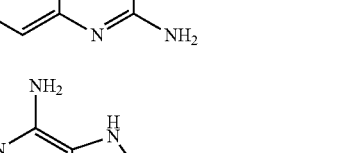 | — |
| Resiquimod | 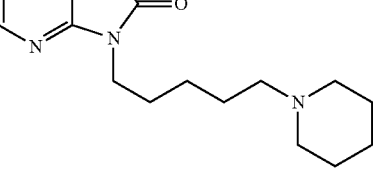 | — |
| Vesatolimod | 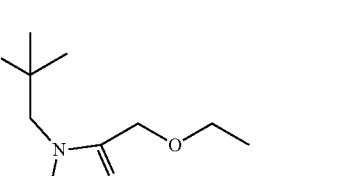 | — |
| Telratolimod | 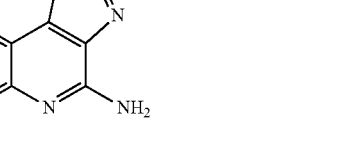 | — |

| Name/Number | Structural formula | Chemical name |
|---|---|---|
| TMX-202 | | — |
| DSP-0509 | — | — |
| RG-7854 | — | — |
| Loxoribine | | — |

The term "substitute" or "substituted" means that one or more hydrogen atoms on a specific atom are substituted with substituents, as long as the valence of the specific atom is normal and the resulting compound is stable. When the substituent is oxo (namely =O), it means that two hydrogen atoms are substituted, and oxo is not available on an aromatic group.

The term "optional" or "optionally" means that the subsequently described event or circumstance may, but not necessarily, occur. The description includes instances where the event or circumstance occurs and instances where the event or circumstance does not occur. For example, an ethyl optionally substituted with halogen, means that the ethyl may be unsubstituted ($CH_2CH_3$), monosubstituted (for example, $CH_2CH_2F$), polysubstituted (for example, $CHFCH_2F$, $CH_2CHF_2$ and the like) or fully substituted ($CF_2CF_3$). It will be understood by those skilled in the art that for any groups comprising one or more substituents, any substitutions or substituting patterns which may not exist or cannot be synthesized spatially are not introduced.

$C_{m-n}$ used herein means that the portion has an integer number of carbon atoms in the given range. For example, "$C_{1-6}$" means that the group may have 1 carbon atom, 2 carbon atoms, 3 carbon atoms, 4 carbon atoms, 5 carbon atoms or 6 carbon atoms.

When any variable (e.g., R) occurs more than once in the constitution or structure of a compound, the definition of the variable in each case is independent. Therefore, for example, if a group is substituted with 2 R, the definition of each R is independent.

When a connecting group has a number of 0, for example, —$(CH_2)_0$—, it means that the connecting group is a covalent bond.

When a bond of a substituent is cross-linked to two atoms on a ring, the substituent can be bonded to any atom on the ring. For example, structural unit

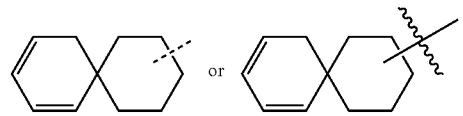

represents that substitution may occur in any one position of cyclohexyl or cyclohexadienyl.

The term "halo-", "halogenated" or "halogen" refers to fluorine, chlorine, bromine and iodine.

The term "hydroxyl" refers to —OH group.
The term "cyano" refers to —CN group.
The term "sulfydryl" refers to —SH group.
The term "amino" refers to —$NH_2$ group.
The term "alkyl" refers to hydrocarbyl with a general formula of $C_nH_{2n+1}$. The alkyl can be linear or branched. For example, the term "$C_{1-6}$ alkyl" refers to alkyl with 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl portions (namely alkyl) of alkoxyl, monoalkylamine, dialkylamine, alkylsulfonyl and alkylsulfanyl have the same meaning as defined above.

The term "alkoxyl" refers to —O-alkyl.
The term "alkenyl" refers to linear or branched unsaturated aliphatic hydrocarbyl consisting of carbon atoms and hydrogen atoms with at least one double bond. Non-limiting examples of alkenyl include, but are not limited to, ethenyl, 1-propenyl, 2-propenyl, 1-butenyl, isobutenyl, 1,3-butadienyl, and the like.

The term "alkynyl" refers to linear or branched unsaturated aliphatic hydrocarbyl consisting of carbon atoms and hydrogen atoms with at least one triple bond. Non-limiting examples of alkynyl include, but are not limited to, acetenyl (—C≡CH), 1-propinyl (—C≡C—CH$_3$), 2-propinyl (—CH$_2$—C≡CH), 1,3-butadiynyl (—C≡C—C≡CH) and the like.

The term "cycloalkyl" refers to a fully saturated carbocycle that can exist in the form of a monocycle, bridged cycle or spiro cycle. Unless otherwise specified, the carboncycle is generally a 3-10 membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl and the like.

The term "cyclohydrocarbyl" refers to a saturated or unsaturated nonaromatic cyclic hydrocarbyl consisting of carbon atoms and hydrogen atoms, preferably including 1 or 2 rings. The cyclohydrocarbyl can be of monocyclic, fused polycyclic, bridged cyclic or spiro structures. Non-limiting examples of cyclohydrocarbyl include, but are not limited to, cyclopropyl, cyclobutyl, cyclopentyl, cyclohexyl, cycloheptyl, bicyclo[2.2.1]heptyl, spiro[3.3]heptyl and the like.

The term "heterocyclohydrocarbyl" refers to a nonaromatic monocyclic, fused polycyclic, bridged cyclic or spiro cyclic group, wherein some ring atoms are heteroatoms selected from the group consisting of N, O, and S(O)$_n$ (n is 0, 1 or 2), while the remaining ring atoms are C. Such a ring can be saturated or unsaturated (for example, with one or more double bonds), but does not have a fully conjugated 7-electron system. Examples of 3 membered heterocyclohydrocarbyl include, but are not limited to, oxiranyl, thiiranyl and aziranyl. Examples of 4 membered heterocyclohydrocarbyl include, but are not limited to, azetidinyl, oxetanyl and thietanyl. Examples of 5 membered heterocyclohydrocarbyl include, but are not limited to, tetrahydrofuranyl, tetrahydrothienyl, pyrrolidinyl, isoxazolidinyl, oxazolidinyl, isothiazolidinyl, 1,1-dioxidoisothiazolidinyl, thiazolidinyl, imidazolidinyl, tetrahydropyrazolyl, pyrrolinyl, dihydrofuranyl and dihydrothienyl. Examples of 6 membered heterocyclohydrocarbyl include, but are not limited to, piperidinyl, tetrahydropyranyl, tetrahydrothiapyranyl, morpholinyl, piperazinyl, 1,4-oxathianyl, 1,4-dioxanyl, thiomorpholinyl, 1,2- and 1,4-dithianyl, dihydropyridinyl, tetrahydropyridinyl, dihydropyranyl, tetrahydropyranyl and dihydrothiapyranyl. Examples of 7 membered heterocyclohydrocarbyl include, but are not limited to, azacycloheptanyl, oxacycloheptanyl, thiocycloheptanyl, oxaazabicyclo[2.2.1]heptyl, azaspiro[3.3]heptyl and the like.

The term "aryl" refers to an aromatic monocyclic or fused polycyclic group of carbon atoms with the fully conjugated π-electron system. For example, an aryl may have 6-20 carbon atoms, 6-14 carbon atoms or 6-12 carbon atoms. Non-limiting examples of aryl include, but are not limited to, phenyl, naphthyl, anthryl, 1,2,3,4-tetrahydronaphthalenyl, and the like.

The term "heteroaryl" refers to a monocyclic or fused polycyclic system which comprises at least one ring atom selected from the group consisting of N, O and S, with the remaining ring atoms being C, and which has at least one aromatic ring. Preferably, heteroaryl has a single 4-8 membered ring, in particular, a 5-8 membered ring, or comprises a plurality of fused rings comprising 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl and the like.

The term "treatment" usually refers to acquiring needed pharmacological effect and/or physiological effect. In terms of fully or partially preventing a disease or a symptom thereof, the effect can be preventive; and/or in terms of partially or fully stabilizing or curing the disease and/or a side effect of the disease, the effect can be therapeutic. "Treatment" used therein covers any treatment to a disease in a patient, including (a) preventing a disease or a symptom of a disease from occurring in a patient which may be predisposed to the disease but has not yet been diagnosed as suffering from it; (b) inhibiting a symptom of a disease, i.e., arresting its development; or (c) relieving a symptom of a disease, i.e., causing regression of a disease or a symptom.

The term "effective amount" refers to an amount of the compound disclosed herein for (i) treating or preventing a specific disease, condition or disorder; (ii) alleviating, relieving or eliminating one or more symptoms of a specific disease, condition or disorder, or (iii) preventing or delaying onset of one or more symptoms of a specific disease, condition or disorder. The amount of the compound disclosed herein composing the "therapeutically effective amount" varies dependently on the compound, the disease state and its severity, the administration regimen, and the age of the mammal to be treated, but can be determined routinely by those skilled in the art in accordance with their knowledge and the present disclosure.

As used herein, the compound of formula I or the pharmaceutically acceptable salt thereof may be administered by any applicable routes and methods, for example, oral administration or parenteral (for example, intravenous) administration. The therapeutically effective amount of the compound of formula I or the pharmaceutically acceptable salt thereof includes, but is not limited to, from about 0.0001 mg/kg/d to 20 mg/kg/d, for example, from 0.001 mg/kg/d to 10 mg/kg/d. The dosage and administration frequency of the compound of formula I depend on needs of an individual patient, for example, once daily, twice daily, or more times daily. Administration can be intermittent, for example, in a period of several days, the patient receives a daily dosage of the compound of formula I, and in the following period of the several days or more days, the patient does not receive the daily dosage of the compound of formula I.

Anlotinib can be administered in various routes including, but not limited to, oral, parenteral, intraperitoneal, intravenous, intra-arterial, transdermal, sublingual, intramuscular, rectal, transbuccal, intranasal, inhalational, vaginal, intraocular, topical, subcutaneous, intralipid, intra-articular and intrathecal administrations. In some specific embodiments, anlotinib is orally administered. The dosing amount of anlotinib can be determined according to the severity of the disease, the response of the disease, any treatment-related toxicity, and the age and health of a patient. For example, the daily dosage of anlotinib can be 2 mg to 20 mg. In some embodiments, the daily dosage of the compound of formula I or the pharmaceutically acceptable salt thereof can be 2 mg, 3 mg, 4 mg, 5 mg, 6 mg, 7 mg, 8 mg, 9 mg, 10 mg, 11 mg, 12 mg, 13 mg, 14 mg, 15 mg and 16 mg. Anlotinib can be administered once or multiple times daily. In one embodiment, anlotinib is administered once daily in the form of a solid oral preparation.

The dosage regimen of anlotinib can be determined comprehensively depending on the activity and toxicity of the medicament, tolerance of the patient, etc. Preferably, anlotinib is administered in an intermittent regimen. The intermittent regimen comprises a treatment period and an interruption period. In the treatment period, anlotinib can be administered once or multiple times daily. For example, the ratio of the treatment period to the interruption period in days is 2:0.5-2:5, preferably 2:0.5-2:3, more preferably 2:0.5-2:2, and most preferably 2:0.5-2:1. In some embodiments, anlotinib is administered for 2 weeks and interrupted for 2 weeks. In some embodiments, anlotinib is administered for 2 weeks and interrupted for 1 week. In some embodiments, anlotinib is administered for 5 days and interrupted for 2 days. For example, anlotinib can be administered once daily at a dosage of 6 mg, 8 mg, 10 mg or 12 mg for 2 weeks, and interrupted for 1 week.

As used herein, the TLR7 agonist and anlotinib include non-salt forms thereof (for example, free acids or free base) and further include pharmaceutically acceptable salts thereof. The non-salt forms or salt forms fall within the protection scope of the present application. For example, the pharmaceutically acceptable salts of the TLR7 agonist can be hydrochloride and the pharmaceutically acceptable salts of anlotinib can be hydrochloride or dihydrochloride.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" includes salts formed from a basic radical and a free acid and salts formed from an acidic radical and a free base, for example, hydrochloride, hydrobromide, nitrate, sulfate, phosphate, formate, acetate, trifluoroacetate, fumarate, oxalate, maleate, citrate, succinate, mesylate, benzenesulfonate and p-methylbenzenesulfonate, preferably, hydrochloride, hydrobromide, sulfate, formate, acetate, trifluoroacetate, fumarate, maleate, mesylate, p-methylbenzenesulfonate, sodium salt, potassium salt, ammonium salt and amino acid salt and so on. In the present application, when forming a pharmaceutically acceptable salt, the free acid and the basic radical are in a molar weight ratio of about 1:0.5 to 1:5, preferably, 1:0.5, 1:1, 1:2, 1:3, 1:4, 1:5, 1:6, 1:7 or 1:8. In the present application, when forming a pharmaceutically acceptable salt, the free base and the acidic radical are in a molar weight ratio of about 1:0.5 to 1:5, preferably, 1:0.5, 1:1, 1:2, 1:3, 1:4, 1:5, 1:6, 1:7 or 1:8.

As used herein, if the compound in the pharmaceutical combination has, for example, at least one basic site, an acid addition salt may be formed. If needed, it may further form an acid addition salt with additional existing basic sites. A compound with at least one acidic group (for example, —COOH) can further form a salt with a base. A compound, for example, comprising both carboxyl and amino, can further form an inner salt.

The compound disclosed herein can be asymmetrical, for example, has one or more stereoisomers. Unless otherwise stated, all stereoisomers are included, for example, enantiomers and diastereoisomers. The compound with asymmetrical carbon atoms disclosed herein can be separated in an optically pure form or in a racemic form. The optically pure form can be separated from a racemic mixture or can be synthesized using a chiral raw material or a chiral reagent.

The term "subject" is a mammal. In some embodiments, the subject is a mouse. In some embodiments, the subject is a human.

The term "about" shall be understood to include a range of three standard deviations from a mean value or a standard tolerance range in a specific field. In some embodiments, the term "about" shall be understood as a variation not exceeding 0.5. The term "about" modifies all listed values thereafter. For example, "about 1, 2 and 3" represents "about 1", "about 2" and "about 3".

The term "pharmaceutical combination" refers to simultaneous, parallel or sequentially combined use of two or more active ingredients. The pharmaceutical combination allows the active ingredients to demonstrate a cooperation (combination) effect. In some embodiments, the effect is a synergistic effect. The pharmaceutical combination includes fixed combination or non-fixed combination.

The term "fixed combination" refers to administration of the active ingredients (for example, the TLR7 agonist or anlotinib) to an individual simultaneously at a fixed total dosage or in a fixed dosage proportion, or in the form of a single substance, pharmaceutical composition or formulation. In other words, the active ingredients are present in one pharmaceutical formulation. In some embodiments, for example, the active ingredients are present in one tablet, one capsule, or one bag.

The term "non-fixed combination" refers to simultaneous, parallel or sequential (without specific time limitation) administration of two or more active ingredients as independent entities (for example, a pharmaceutical composition and a pharmaceutical formulation) to a subject, wherein the active ingredients administered to the subject reach therapeutically effective amounts. An example, which can be enumerated, of the non-fixed combination is a cocktail therapy, for example, 3 or more active ingredients are administered. In a non-fixed combination, each active component can be packaged, sold or administered as a fully independent pharmaceutical composition. The "non-fixed combination" further includes combined use of "fixed combinations", or a "fixed combination" and an independent substance of any one or more active ingredients.

The term "pharmaceutical composition" refers to a mixture consisting of one or more of the compounds or pharmaceutically acceptable salts thereof or the pharmaceutical combination or salts thereof disclosed herein, and a pharmaceutically acceptable excipient. The pharmaceutical composition is intended to facilitate the administration of the compound or the pharmaceutical combination thereof disclosed herein to an individual.

The term "synergistic effect" means that the effect (for example, inhibiting the growth of colorectal cancer cells or alleviating the symptoms of colorectal cancer) produced by a combination of two active ingredients (for example, the TLR7 agonist and anlotinib) is superior to the simple addition of the effect produced by the two active ingredients separately.

Administration Mode

The content below is not intended to limit the administration of the pharmaceutical combination disclosed herein.

The active ingredients in the pharmaceutical combination disclosed herein can be formulated separately, or some or all of the active ingredients are co-formulated. In one embodiment, the pharmaceutical combination disclosed herein can be formulated into a pharmaceutical composition which is suitable for a single dose or multiple doses.

The active ingredients in the pharmaceutical combination disclosed herein can be administered separately, or some or all of the active ingredients are co-administered. The active ingredients in the pharmaceutical combination disclosed herein can be administered in a substantially asynchronous manner, or some or all of the active ingredients are administered in a substantially synchronous manner.

The active ingredients in the pharmaceutical combination disclosed herein can be administered independently, or some or all of the active ingredients are co-administered in various proper routes, including, but not limited to, oral administration or parenteral administration (intravenous, intramuscular, local or subcutaneous routes). In some embodiments, the active ingredients in the pharmaceutical combination disclosed herein can be administered independently, or some or all of the active ingredients are co-administered by means of oral administration or injection, for example, intravenous injection or intraperitoneal injection.

The active ingredients in the pharmaceutical combination disclosed herein can be independent suitable dosage forms, or some or all of the active ingredients are co-formulated in a suitable dosage form, including, but not limited to, tablet, lozenge, pill, capsule (for example, hard capsule, soft capsule, enteric capsule and microcapsule), elixir, granule, syrup, injection (intramuscular, intravenous and intraperitoneal), powder, emulsion, suspension, solution, dispersant and dosage forms of slow-released preparations for oral or non-oral administration.

The active ingredients in the pharmaceutical combination disclosed herein can be formulated independently, or some or all of the active ingredients are co-formulated with a pharmaceutically acceptable carrier and/or excipient.

The pharmaceutical combination may further comprise an additional therapeutic agent. In one embodiment, the additional therapeutic agent can be a known therapeutic agent for cancer in the art, preferably a therapeutic agent for colorectal cancer.

In embodiments of the present application, the dosages are all calculated as per the free base form of the compounds.

Technical Effects

The inventors have surprisingly found that the compound of formula I as the TLR7 agonist or the pharmaceutically acceptable salt thereof has good efficacy against colorectal cancer. Further, the pharmaceutical combination of the TLR7 agonist and anlotinib also has good efficacy against colorectal cancer.

DETAILED DESCRIPTION

For clarity, the present application is further described with the following examples, which are, however, not intended to limit the scope of the present application. All reagents used in the present application are commercially available and can be used without further purification.

A method for preparing the compound of formula I of the present application and its in vitro binding activity to a toll-like receptor 7 can be seen in WO2016023511 and WO2017076346.

Example 1 Anti-Tumor Experiment in MC-38 Mouse Model

In Example 1, the TLR7 agonist is selected from

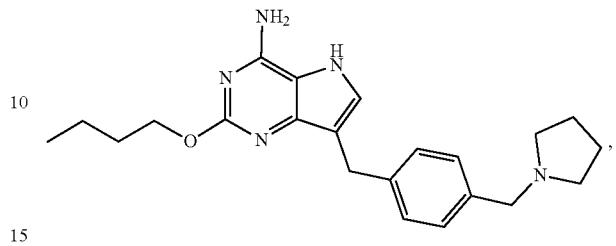

and anlotinib is selected from anlotinib dihydrochloride.

The MC-38 is a colon cancer cell of mouse from Jiangsu Cyto Biotechnology Co., Ltd.

Subcutaneously grafted tumor cells of MC-38 colon cancer (concentration: $2\times10^6$/mL$\times$0.2 mL/mouse) were inoculated into female C57BL/6 mice at the right side armpit (the site to be inoculated was shaved before inoculating) in a sterile environment, and passaged using a block insertion method. The C57BL/6 mice were 16-18 g in weight, and the breeding environment was SPF level. The diameter of the C57BL/6 xenograft tumor was measured using a vernier caliper, and the mice were randomized into 4 groups when the tumors grew to 100-300 mm$^3$ (12 mice for control group and 6 mice each for other groups):

i. Control group (blank control);
ii. Monotherapy group: anlotinib, with normal saline as vehicle;
iii. Monotherapy group: TLR7 agonist, with ethanol+tween 80+normal saline (v:v:v=5:5:90) as vehicle;
iv. Combination therapy group: TLR7 agonist+anlotinib.

TABLE 1

| | Administration regimen | | | |
|---|---|---|---|---|
| Group | Dosage mg/kg/time | Route of administration | Administration interval | Administration period |
| i. | — | i.g. | qd | 2 w |
| ii. | 1 | i.g. | qd | 2 w |
| iii. | 20 | i.g. | tiw | 2 w |
| iv. | 1 (Anlotinib) | i.g. | qd | 2 w |
| | 20 (TLR7 agonist) | i.g. | tiw | 2 w | i.g.: intragastric administration;
qd: administration once daily;
tiw: thrice a week.

The administration method of the combination therapy group is consistent with that of the monotherapy group.

Weights and diameter of the tumor were measured every three days, and the behavior of mice was observed daily. After the experiment was completed, the tumors were removed, weighed and photographed.

The tumor volume and the tumor growth inhibition were calculated using the following formulas:

Tumor volume (TV)=($L\times W^2$)/2.

Tumor growth inhibition (TGI)(%)=(1−tumor weight in treatment group/tumor weight in control group)$\times$100%.

The results as shown in Table 2 indicate that the TLR7 agonist can inhibit the growth of MC-38 tumor, and its combined use with anlotinib dihydrochloride can also inhibit the growth of MC-38 tumor with a synergistic effect.

TABLE 2

Experiment results for subcutaneous xenograft tumor of MC-38 colon cancer in mice

| Group | TV (mm³) on day 0 Mean ± SD | TV (mm³) on day 12 Mean ± SD | TV (mm³) on day 18 Mean ± SD | TGI (%) |
|---|---|---|---|---|
| i. | 143.06 ± 35.90 | 717.08 ± 362.31 | 1325.98 ± 595.27 | — |
| ii. | 143.28 ± 45.46 | 427.30 ± 135.63 | 900.32 ± 346.06 | 33 |
| iii. | 143.93 ± 47.74 | 427.88 ± 161.31 | 747.63 ± 347.13 | 39 |
| iv. | 143.76 ± 46.04 | 191.00 ± 88.72 | 415.74 ± 183.33 | 69 |

The TGI (%), as a value of efficacy, was substituted into the Jin zhengjun's formula q=Eab/(Ea+Eb−Ea×Eb), where Ea and Eb represent the efficacy of medicaments used alone, and Eab represents the efficacy of combined use. The obtained q value is more than 1.15, showing synergistic effect of combined use.

The invention claimed is:

1. A method for inhibiting or relieving a symptom of colorectal cancer, arresting development of colorectal cancer or causing regression of colorectal cancer or a symptom thereof, comprising administering to a subject in need thereof an effective amount of a pharmaceutical combination comprising one or more TLR7 agonists and anlotinib or a pharmaceutically acceptable salt thereof, wherein the TLR7 agonist comprises 2-butoxy-7-(4-(pyrrolidin-1-ylmethyl) benzyl)-5H-pyrrolo[3,2-d] pyrimidin-4-amine having the structure

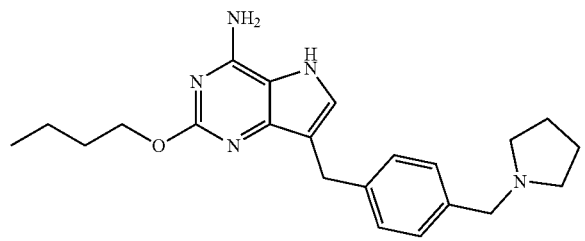

or a pharmaceutically acceptable salt thereof.

2. The method according to claim 1, wherein the pharmaceutical combination is selected from the group consisting of a fixed combination and a non-fixed combination.

3. The method according to claim 2, wherein the fixed combination is in the form of a solid pharmaceutical composition, and the non-fixed combination are each in the form of a solid pharmaceutical composition.

4. The method according to claim 3, wherein the solid pharmaceutical composition is selected from the group consisting of a tablet and a capsule.

5. The method according to claim 1, wherein the colorectal cancer is selected from the group consisting of colon cancer and rectal cancer.

6. The method according to claim 1, wherein anlotinib is anlotinib dihydrochloride.

7. The method according to claim 6, wherein the TLR7 agonist is administered in a dosage of 0.001 mg/kg/d to 10 mg/kg/d, and anlotinib dihydrochloride is administered in a dosage of 6 mg/d, 8 mg/d, 10 mg/d, 12 mg/d, 14 mg/d, 16 mg/d.

8. The method according to claim 6, wherein the TLR7 agonist is administered in a dosage of 0.001 mg/kg/d to 10 mg/kg/d, and anlotinib dihydrochloride is administered in a dosage of 10 mg/d to 14 mg/d.

9. The method according to claim 6, wherein the TLR7 agonist is administered thrice a week at 0.0001 mg/kg/dose to 20 mg/kg/dose, and anlotinib dihydrochloride is administered in a dosage of 6 mg/d to 16 mg/d for 2 weeks continuously.

10. The method according to claim 6, wherein the TLR7 agonist is administered thrice a week at 0.001 mg/kg/time to 10 mg/kg/time, and anlotinib dihydrochloride is administered in a dosage of 6 mg/d, 8 mg/d, 10 mg/d, 12 mg/d, 14 mg/d, 16 mg/d for 2 weeks continuously.

11. The method according to claim 6, wherein the TLR7 agonist is administered thrice a week at 0.001 mg/kg/time to 10 mg/kg/time, and anlotinib dihydrochloride is administered in a dosage of 10 mg/d to 14 mg/d for 2 weeks continuously.

12. The method according to claim 6, wherein the TLR7 agonist is administered in a dosage of 0.0001 mg/kg/d to 20 mg/kg/d, and anlotinib dihydrochloride is administered in a dosage of 1 mg/kg/d.

13. The method according to claim 6, wherein the TLR7 agonist is administered in a dosage of 0.001 mg/kg/d to 10 mg/kg/d, and anlotinib dihydrochloride is administered in a dosage of 1 mg/kg/d.

14. The method according to claim 1, wherein the TLR7 agonist is administered in a dosage of 0.0001 mg/kg/d to 20 mg/kg/d, and anlotinib or a pharmaceutically acceptable salt thereof is administered in a unit dosage of 6 mg/d to 16 mg/d.

15. The method according to claim 1, wherein the TLR7 agonist and anlotinib are administered separately.

* * * * *